United States Patent
Mao et al.

(10) Patent No.: US 6,238,687 B1
(45) Date of Patent: *May 29, 2001

(54) BIODEGRADABLE POLYMERS, COMPOSITIONS, ARTICLES AND METHODS FOR MAKING AND USING THE SAME

(75) Inventors: Hai-Quan Mao, Towson; Kam W. Leong, Ellicott City, both of MD (US)

(73) Assignee: Johns Hopkins University School of Medicine, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 09/286,713

(22) Filed: Apr. 5, 1999

Related U.S. Application Data

(63) Continuation-in-part of application No. PCT/US98/07585, filed on Apr. 14, 1998, which is a continuation-in-part of application No. 08/834,164, filed on Apr. 14, 1997, now Pat. No. 5,912,225.

(51) Int. Cl.[7] ............................... A61F 2/02; A61K 47/30
(52) U.S. Cl. .................... 424/426; 424/424; 424/425; 514/772.3
(58) Field of Search .............................. 424/424, 425, 424/426; 514/772.3

(56) References Cited

U.S. PATENT DOCUMENTS

| | | |
|---|---|---|
| 3,927,231 | 12/1975 | Desitter et al. . |
| 3,932,566 | 1/1976 | Reader . |
| 4,259,222 | 3/1981 | Login et al. . |
| 4,293,539 | 10/1981 | Ludwig et al. . |
| 4,315,847 | 2/1982 | Login et al. . |
| 4,315,969 | 2/1982 | Login et al. . |
| 4,638,045 | 1/1987 | Kohn et al. . |
| 5,099,060 | 3/1992 | Kohn et al. . |
| 5,104,947 | 4/1992 | Schacht et al. . |
| 5,176,907 | 1/1993 | Leong . |
| 5,194,581 | 3/1993 | Leong . |
| 5,219,564 | 6/1993 | Zalipsky et al. . |
| 5,256,765 | 10/1993 | Leong . |
| 5,530,093 | 6/1996 | Engelhardt et al. . |
| 5,626,862 | 5/1997 | Brem et al. . |
| 5,637,085 | 6/1997 | Cardinale . |
| 5,650,442 | 7/1997 | Mitchell et al. . |
| 5,651,986 | 7/1997 | Brem et al. . |
| 5,869,103 | 2/1999 | Yeh et al. . |
| 5,912,225 | 6/1999 | Mao et al. ........................... 514/2 |

FOREIGN PATENT DOCUMENTS

| | | |
|---|---|---|
| 597473 | 5/1960 | (CA) . |
| 0 386 757 | 9/1990 | (EP) . |
| WO 95/35097 | 12/1995 | (WO) . |
| WO 96/02655 | 2/1996 | (WO) . |
| WO 98/27975 | 7/1998 | (WO) . |
| WO 98/46286 | 10/1998 | (WO) . |

OTHER PUBLICATIONS

Williams et al., "Polymers for IUdR Radiosensitization of Experimental Glioblastoma," Society Neuro Oncoloty Abstract: Post Nov. 1997 Meeting.

(List continued on next page.)

Primary Examiner—Carlos A. Azpuru
(74) Attorney, Agent, or Firm—Foley, Hoag & Eliot LLP

(57) ABSTRACT

Biodegradable polymer compositions that degrade in vivo into non-toxic residues are described. In part, the present invention is directed to such polymers containing phosphorus and desaminotyrosyl L-tyrosine linkages in the polymer backbone. Processes for preparing such polymers, compositions containing such polymers and biologically active substances, articles useful for implantation or injection into the body fabricated from the compositions, and methods for controllably releasing biologically active substances using the polymers, are also described.

72 Claims, 2 Drawing Sheets

OTHER PUBLICATIONS

Williams et al., "Implantable Biodegradable Polymers for IUdR Radiosensitization of Human Malignant Glioma In Vivo," American Radium Society Abstract: Podium Presentation 1996 San Francisco.

Williams et al., "Implantable Biodegradable Polymers for IUdR Radiosensitization of Human Malignant Glioma In Vivo," American Society for Clinical Oncology Annual Meeting 1995 Poster Presentation (Abstract).

Williams et al., "Polymers for IUdR Radiosensitization of Experimental Glioblastoma," Congress of Neurological Surgeons Abstract: 1997.

Williams et al. "Implantable Biodegradable Polymers for Radiosensitization of Human Glioma in Vivo," American Society for Therapeutic Radiation and Oncology: Abstract Annual Meeting 1997.

Williams et al. "Implantable Biodegradable Polymers for IUdR Radiosensitization of Human Glioma in Vivo," American Society for Therapeutic Radiation and Oncology: Abstract Annual Meeting 1997.

Williams et al., "Controlled Release of Radiochemicals from Implantable Biodegradable Polymer Devices," Society Nuclear Medicine Abstract.

Van Gool et al., "Overexpression of human poly(ADP–ribose) polymerase in transfected hamster cells leads to increased poly(ADP–ribosyl)ation and cellular sensitization to γ irridation," Eur. J. Biochem 244:15–20 (1997).

Williams et al., "Implantable biodegradable polymers for IUdR radiosensitization of experimental human malignant glioma," Journal of Neuro–Oncology 32:181–192 (1997).

Williams et al. "Combined intracranial iudr polymers and 125–l seets for radiosensitizatio of experimental malignant glioma brachytherapy," American Society for Therapeutic Radiation and Oncology Abstract Annual Meeting 1997.

Mao et al., "Biodegradable Copolymer for Drug Delivery: Poly(phosphate–terephthalate)s," Proceedings of the Topical Conference on Biomaterials Carriers for Drug Delivery and Scaffold for Tissue Engineering, Peppas, N.A., et al. eds. Los Angeles, CA, pp. 141–143 (1997).

Mao et al., "Design of New Biodegradable Polymers Based on Chain–Extension of Oligomeric Lactides by Phosphates," Proceedings of the Topical Conference on Biomaterials Carriers for Drug Delivery and Scaffold for Tissue Engineering, Peppas, N.A., et al., eds. Los Angeles, CA, pp. 193–195 (1997).

Pretula et al., "High–molecular–weight poly(alkylene phosphonate)s by condensation of dialkylphosphonates with diols," Die Makromolekulare Chemis 191:671–680 (1990).

Bruin et al., "Biodegradable Lysine Diisocyanate–based Poly(glycolide– co–ϵ– caprolactone)—urethane Network in Artificial Skin", Biomaterials, 11 (4): 291–295 (1990).

Chien, Y. W. et al., Novel Drug Delivery Systems (1982).

Choueka et al., "Canine Bone Response to Tyrosine–derived Polycarbonates and Poly( L– lactic Acid)", Journal of Biomedical Materials Research, 31 : 35–41 (1996).

Ertel et al., "Evaluation of Poly( DTH Carbonate), a Tyrosine– derived Degradable Polymer, for Orthopedic Applications", Journal of Biomedical and Materials Research, 29: 1337–1348 (1995).

Kadiyala et al., "Poly ( phosphoesters): Synthesis, Physico–chemical Characterization and Biological Response", Biomedical Applications of Synthesic Biodegradable Polymers, Chpt. 3, 33–55 (Hollinger ed. 1995).

Langer et al., "Controlled Release of Bioactive Agents", Rev. Macro. Chem. Phys., C23 (1), 61–125 (1983).

Langer et al., "New Methods of Drug Delivery", Science, 249 (4976): 1527–1533 (1990).

Leong et al., "Polyanhydrides for Controlled Release of Bioactive Agents", Biomaterial:364 (1986).

Leong et al., "Polymeric Controlled Drug Delivery", Advanced Drug Delivery Reviews, 1, :199–233 (1987).

Penczek et al., "Phosphorus– Containing Polymers", Handbook of Polymer Synthesis, Part B, Chpt 17, pp. 1077–1132 (Kricheldorf ed. 1992).

Pulapura et al., "Trends in the Development of Bioresorbable Polymers for Medical Applications", Journal of Biomaterials Applications, 6 (1) :216–250 (1992).

BIODEGRADABLE POLYMERS, COMPOSITIONS, ARTICLES AND METHODS FOR MAKING AND USING THE SAME

PRIORITY

This application is a continuation-in part of application Ser. No. 08/834,164, filed Apr. 14, 1997, now U.S. Pat. No. 5,912,225, and claims benefit of priority of International Application PCT/US98/07585, filed Apr. 14, 1998.

BACKGROUND OF THE INVENTION

1. Introduction

The present invention relates in part to biodegradable polymer compositions, in particular those containing phosphorus and desaminotyrosyl L-tyrosine linkages in the polymer backbone and that degrade in vivo into non-toxic residues. In certain embodiments, the polymers of the invention are particularly useful as implantable medical devices and drug delivery systems.

2. Description of the Prior Art

Biocompatible polymeric materials have been used extensively in therapeutic drug delivery and medical implant device applications. Sometimes, it is also desirable for such polymers to be, not only biocompatible, but also biodegradable to obviate the need for removing the polymer once its therapeutic value has been exhausted.

Conventional methods of drug delivery, such as frequent-periodic dosing, are not ideal in many cases. For example, with highly toxic drugs, frequent conventional dosing can result in high initial drug levels at the time of dosing, often at near-toxic levels, followed by low drug levels between doses that can be below the level of their therapeutic value. However, with controlled drug delivery, drug levels can be more nearly maintained at therapeutic, but non-toxic, levels by controlled release in a predictable manner over a longer term.

If a biodegradable medical device is intended for use as a drug delivery or other controlled-release system, using a polymeric carrier is one effective means to deliver the therapeutic agent locally in a controlled fashion (see Langer et al., (1983) *Rev. Macro. Chem. Phys.* C23(1):61). As a result, less total drug is required, and toxic can be minimized. Polymers have been used as carriers of therapeutic agents to effect: a localized and sustained release (see *Controlled Drug Delivery*, Vols. I and II; Bruck et al., eds. (1982); and Chien et al., (1982) *Novel Drug Delivery Systems*). Such delivery systems offer the potential of enhanced therapeutic efficacy and reduced overall toxicity.

For a non-biodegradable matrix, the steps leading to release of the therapeutic agent are water diffusion into the matrix, dissolution of the therapeutic agent, and diffusion of the therapeutic agent out through the channels of the matrix. As a consequence, the mean residence time of the therapeutic agent existing in the soluble state is longer for a non-biodegradable matrix than for a biodegradable matrix, for which passage through the channels of the matrix, while it may occur, is no longer required. Since many pharmaceuticals have short half-lives, therapeutic agents can decompose or become inactivated within the non-biodegradable matrix before they are released. This issue is particularly significant for many bio-macromolecules and smaller polypeptides, since these molecules are generally hydrolytically unstable and have low permeability through a polymer matrix. In fact, in a non-biodegradable matrix, many bio-macromolecules aggregate and precipitate, blocking the channels necessary for diffusion out of the carrier matrix.

These problems are alleviated by using a biodegradable matrix that, in addition to some diffusional release, also allows controlled release of the therapeutic agent by degradation of the polymer matrix. Examples of classes of synthetic polymers that have been studied as possible biodegradable materials include polyesters (Pitt et al., (1980) *Controlled Release of Bioactive Materials*, Baker, ed.), polyamides (Sidman et al., (1979) *J. of Membrane Sci.*, 7:227), polyurethanes (Maser et al., (1979) *J. of Polymer Sci.*, 66:259), polyorthoesters (Heller, et al. (1981) *Polymer Engineering Sci.*, 21:7271), and polyanhydrides (Leong et al. (1986) *Biomaterials*, 7:364). Specific examples of biodegradable materials that are used as medical implant materials are polylactide, polyglycolide, polydioxanone, poly(lactide-co-glycolide), poly(glycolide-co-polydioxarone), polyanhydrides, poly(glycolide-co-trimethylene carbonate), and poly(glycolide-co-caprolactone).

Polymers having phosphate linkages, called poly(phosphates), poly(phosphonates) and poly(phosphites), are known. (See Butler, (1967) Reviews in *Macromolecular Chemistry*, Dekker, ed., Vol.2, 91–177). The respective structures of these three classes of compounds, each having a different sidechain connected to the phosphorus atom, are as follows:

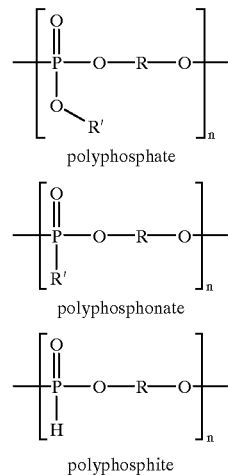

The versatility of these polymers comes from the versatility of the phosphorus atom, which is known for a multiplicity of reactions. Its bonding can involve the 3p orbitals or various 3s-3p hybrids; spd hybrids are also possible because of the accessible d orbitals. Thus, the physicochemical properties of the poly(phosphoesters) can be readily changed by varying either the R or R' group. The biodegradability of the polymer is due primarily to the physiologically labile phosphoester bond in the backbone of the polymer. By manipulating the backbone or the sidechain, a wide range of biodegradation rates are attainable.

An additional feature of poly(phosphoesters) is the availability of functional side groups. Because phosphorus can be pentavalent, drug molecules or other biologically active substances can be chemically linked to the polymer, as shown by Leong, U.S. Pat. Nos. 5,194,581 and 5,256,765. For example, drugs with -0-carboxy groups may be coupled to the phosphorus via an ester bond, which is hydrolyzable. The P-O-C group backbone also lowers the glass transition temperature of the polymer and, importantly, confers solubility in common organic solvents, which is desirable for easy characterization and processing.

Kohn et al., U.S. Pat. No. 4,638,045, discloses bioerodible polymers comprising monomer units of two or three amino acids polymerized via hydrolytically labile bonds at their respective sidechains, rather than at the amino- or carboxylic acid-terminals by amide bonds. Zalipsky et al., U.S. Pat. No. 5,219,564, discloses copolymers of poly(alkylene oxides) and amino acids having pendent fuinctional groups capable of being conjugated with pharmaceutically active compounds for drug delivery systems.

Kohn et al., U.S. Pat. No. 5,099,060, describes a particularly preferred monomer for making amino-acid derived poly(iminocarbonates) as:

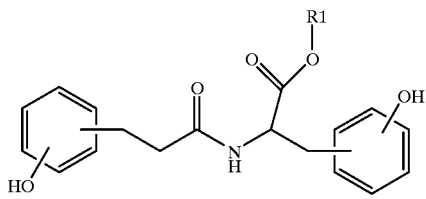

The resulting poly(iminocarbonate) type polymers are said to be hydrolytically unstable and yet exhibit improved thermal stability for convenient processing. Similar tyrosine-derived poly(carbonate) compounds have been reported as promising orthopedic implant materials. (Ertel et al., (1995) *J. Biomedical Materials Res.* 29:1337–1348; and Choueka et al., (1996) *J. Biomed. Materials Res.*, 31:35–41). However, there has been a need for materials to degrade at a significantly higher rate than desaminotyrosyl L-tyrosine based poly(iminocarbonates), and none of these documents suggests the use of phosphoester linkages in combination with amino acid-derived monomeric units for this purpose.

SUMMARY OF THE INVENTION

The present invention is directed to a polymer system, methods for therapeutic and/or cosmetic treatment using the polymer system, and a precursor of the polymer system, a liquid composition.

One aspect of the present invention relates to a polymeric composition comprising one or more recurring monomeric elements in the polymer represented in the general formula (I):

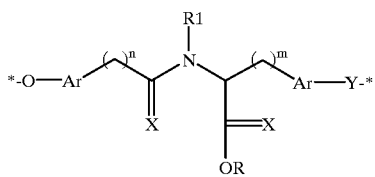

wherein,

Ar, independently for each occurrence, represents an aryl moiety;

X, for each occurrence, represents O or S (preferably O);

Y represents a phosphate, or derivative thereof;

R represents H, an alkyl, an alkenyl, an alkynyl, an aryl or a heterocycle, preferably a branched or straight chain aliphatic group having from 1–20 carbon atoms;

R1 represents H or a lower alkyl; and n and m, independently, are 0, 1, 2 or 3 (preferably 1 or 2).

In the above formula, and others used herein, "*" represents another monomeric unit of the polymer, which can be the same or different from I, or a chain terminating group, e.g., a hydrogen or hydroxyl-protecting group, as appropriate.

In preferred embodiments, the biodegradable polymers of the invention comprise the recurring monomeric units shown in formula III:

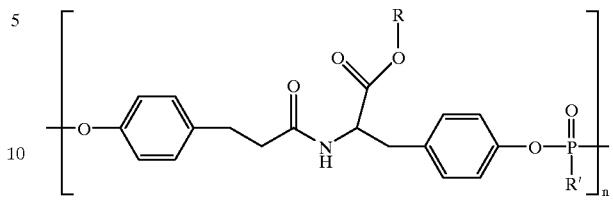

wherein:

R is selected from the group consisting of H, alkyl, aryl or heterocyclic; and

R' is selected from the group consisting of H, alkyl, alkoxy, aryl, aryloxy, heterocyclic or heterocycloxy; and n is 5 to 500, wherein the biodegradable polymer is biocompatible before and upon biodegradation.

In another embodiment, the invention comprises polymer compositions comprising:

(a) at least one biologically active substance and (b) a polymer having the recurring monomeric units shown in formula In yet another embodiment of the invention, an article useful for implantation, injection, or otherwise placed totally or partially within the body, comprises the biodegradable polymer of formula I or the above-described polymer composition.

In a further embodiment, the invention contemplates a process for preparing a biodegradable polymer, comprising the step of reacting an amino acid derivative having fomula IV:

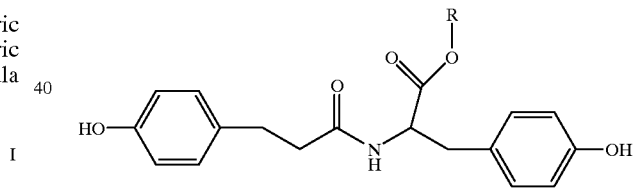

wherein R is as defined above, with a phosphodihalidate of formula V:

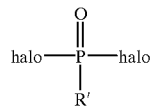

where "halo" is Br, Cl or I, and R' is as defined above, to form the polymer of formula III.

In a still further embodiment of the invention, a method is provided for the controlled release of a biologically active substance comprising the steps of:

(a) combining the biologically active substance with a biodegradable polymer having the recurring monomeric units shown in formula I to form an admixture;

(b) forming the admixture into a shaped, solid article; and (c) implanting or injecting the solid article in vivo at a preselected site, such that the solid implanted or injected article is in at least partial contact with a biological fluid.

In yet another embodiment of the present invention, the polymers and blends can be used as a pharmaceutical carrier in a drug delivery matrix. To form this matrix the polymers and blends can be mixed with a therapeutic agent to form the matrix. The variety of different therapeutic agents which can be used in conjunction with the aliphatic polyoxaesters of the invention is vast. In general, therapeutic agents which may be administered via the pharmaceutical compositions of the invention include, without limitation: antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

Specific examples of bioactive material that can be formulated in the subject polymers in accordance with the present invention include acebutolol, acetaminophen, acetohydoxamic acid, acetophenazine, acyclovir, adrenocorticoids, allopurinol, alprazolam, aluminum hydroxide, amantadine, ambenonium, amiloride, aminobenzoate potassium, amobarbital, amoxicillin, amphetamine, ampicillin, androgens, anesthetics, anticoagulants, anticonvulsants-dione type, antithyroid medicine, appetite suppressants, aspirin, atenolol, atropine, azatadine, bacampicillin, baclofen, beclomethasone, belladonna, bendroflumethiazide, benzoyl peroxide, benzthiazide, benztropine, betamethasone, betha nechol, biperiden, bisacodyl, bromocriptine, bromodiphenhydramine, brompheniramine, buclizine, bumetanide, busulfan, butabarbital, butaperazine, caffeine, calcium carbonate, captopril, carbamazepine, carbenicillin, carbidopa & levodopa, carbinoxamine inhibitors, carbonic anhydsase, carisoprodol, carphenazine, cascara, cefaclor, cefadroxil, cephalexin, cephradine, chlophedianol, chloral hydrate, chlorambucil, chloramphenicol, chlordiazepoxide, chloroquine, chlorothiazide, chlorotrianisene, chlorpheniramine, <a>6X chlorpromazine, chlorpropamide, chlorprothixene, chlorthalidone, chlorzoxazone, cholestyramine, cimetidine, cinoxacin, clemastine, clidinium, clindamycin, clofibrate, clomiphere, clonidine, clorazepate, cloxacillin, colochicine, coloestipol, conjugated estrogen, contraceptives, cortisone, cromolyn, cyclacillin, cyclandelate, cyclizine, cyclobenzaprine, cyclophosphamide, cyclothiazide, cycrimine, cyproheptadine, danazol, danthron, dantrolene, dapsone, dextroamphetamine, dexamethasone, dexchlorpheniramine, dextromethorphan, diazepan, dicloxacillin, dicyclomine, diethylstilbestrol, diflunisal, digitalis, diltiazen, dimenhydrinate, dimethindene, diphenhydramine, diphenidol, diphenoxylate & atrophive, diphenylopyraline, dipyradamole, disopyramide, disulfiram, divalporex, docusate calcium, docusate potassium, docusate sodium, doxyloamine, dronabinol ephedrine, epinephrine, ergoloidmesylates, ergonovine, ergotamine, erythromycins, esterified estrogens, estradiol, estrogen, estrone, estropipute, etharynic acid, etchchlorvynol, ethinyl estradiol, ethopropazine, ethosaximide, ethotoin, fenoprofen, ferrous fumarate, ferrous gluconate, ferrous sulfate, flavoxate, flecainide, fluphenazine, fluprednisolone, flurazepam, folic acid, furosemide, gemfibrozil, glipizide, glyburide, glycopyrrolate, gold compounds, griseofiwin, guaifenesin, guanabenz, guanadrel, guanethidine, halazepam, haloperidol, hetacillin, hexobarbital, hydralazine, hydrochlorothiazide, hydrocortisone (cortisol), hydroflunethiazide, hydroxychloroquine, hydroxyzine, hyoscyamine, ibuprofen, indapamide, indomethacin, insulin, iofoquinol, iron-polysaccharide, isoetharine, isoniazid, isopropamide isoproterenol, isotretinoin, isoxsuprine, kaolin & pectin, ketoconazole, lactulose, levodopa, lincomycin liothyronine, liotrix, lithium, loperamide, lorazepam, magnesium hydroxide, magnesium sulfate, magnesium trisilicate, maprotiline, meclizine, meclofenamate, medroxyproyesterone, melenamic acid, melphalan, mephenytoin, mephobarbital, meprobamate, mercaptopurine, mesoridazine, metaproterenol, metaxalone, methamphetamine, methaqualone, metharbital, methenamine, methicillin, methocarbamol, methotrexate, methsuximide, methyclothinzide, methylcellulos, methyldopa, methylergonovine, methylphenidate, methylprednisolone, methysergide, metoclopramide, metolazone, metoprolol, metronidazole, minoxidil, mitotane, monamine oxidase inhibitors, nadolol, nafcillin, nalidixic acid, naproxen, narcotic analgesics, neomycin, neostigmine, niacin, nicotine, nifedipine, nitrates, nitrofurantoin, nomifensine, norethindrone, norethindrone acetate, norgestrel, nylidrin, nystatin, orphenadrine, oxacillin, oxazepam, oxprenolol, oxymetazoline, oxyphenbutazone, pancrelipase, pantothenic acid, papaverine, para-aminosalicylic acid, paramethasone, paregoric, pemoline, penicillamine, penicillin, penicillin -v, pentobarbital, perphenazine, phenacetin, phenazopyridine, pheniramine, phenobarbital, phenolphthalein, phenprocoumon, phensuximide, phenylbutazone, phenylephrine, phenylpropanolamine, phenyl toloxamine, phenytoin, pilocarpine, pindolol, piper acetazine, piroxicam, poloxamer, polycarbophil calcium, polythiazide, potassium supplements, pruzepam, prazosin, prednisolone, prednisone, primidone, probenecid, probucol, procainamide, procarbazine, prochlorperazine, procyclidine, promazine, promethazine, propantheline, propranolol, pseudoephedrine, psoralens, syllium, pyridostigmine, pyrodoxine, pyrilamine, pyrvinium, quinestrol, quinethazone, uinidine, quinine, ranitidine, rauwolfia alkaloids, riboflavin, rifampin, ritodrine, alicylates, scopolamine, secobarbital, senna, sannosides a & b, simethicone, sodium bicarbonate, sodium phosphate, sodium fluoride, spironolactone, sucrulfate, sulfacytine, sulfamethoxazole, sulfasalazine, sulfinpyrazone, sulfisoxazole, sulindac, talbutal, tamazepam, terbutaline, terfenadine, terphinhydrate, teracyclines, thiabendazole, thiamine, thioridazine, thiothixene, thyroblobulin, thyroid, thyroxine, ticarcillin, timolol, tocainide, tolazamide, tolbutamide, tolmetin trozodone, tretinoin, triamcinolone, trianterene, triazolam, trichlormethiazide, tricyclic antidepressants, tridhexethyl, trifluoperazine, triflupromazine, trihexyphenidyl, trimeprazine, trimethobenzamine, trimethoprim, tripclennamine, triprolidine, valproic acid, verapamil, vitamin A, vitamin B-12, vitamin C, vitamin D, vitamin E, vitamin K, xanthine, and the like.

DETAILED DESCRIPTION OF THE INVENTION

1. Overview

Figure 1:
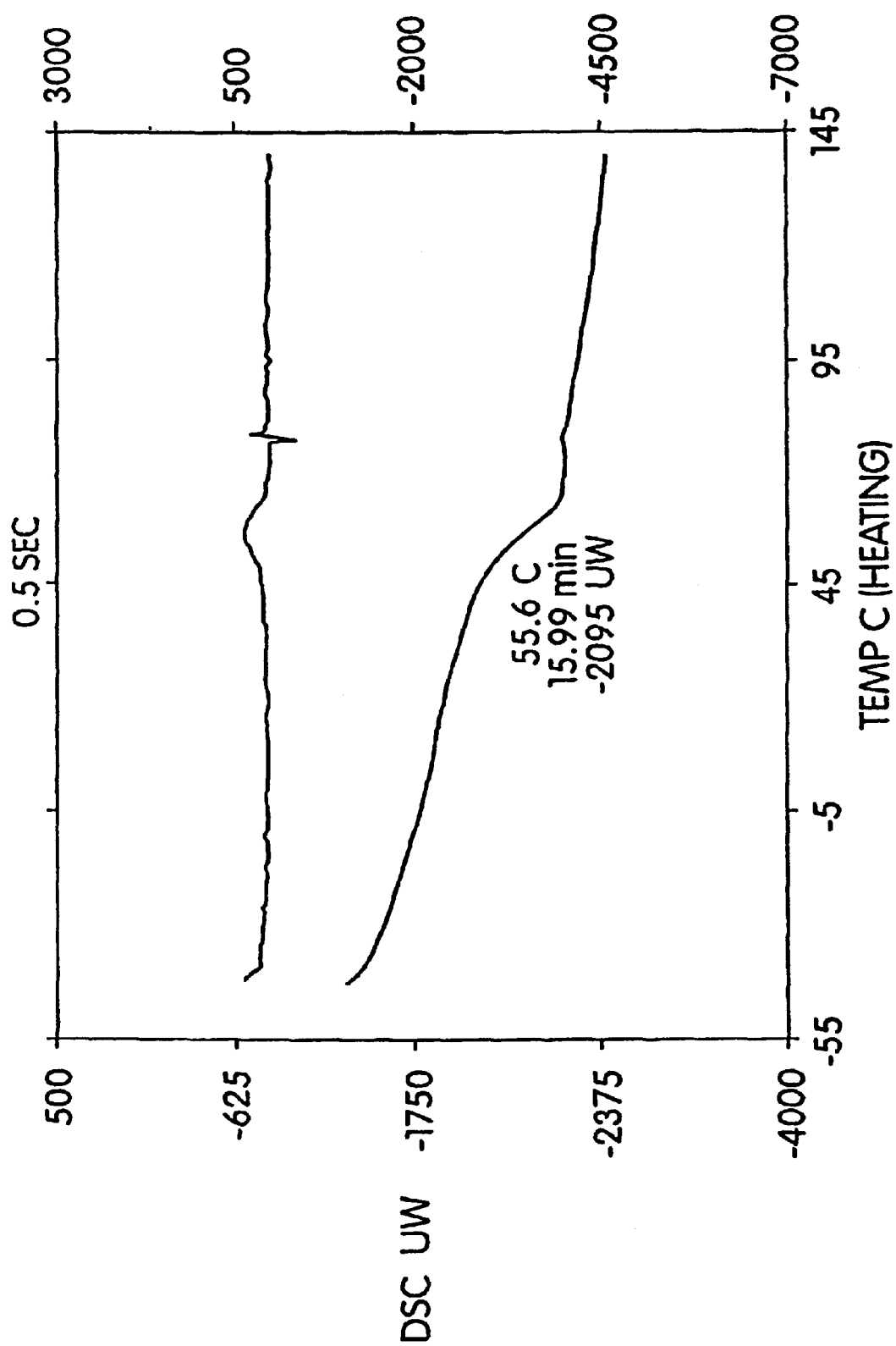
FIG. 1 shows the differential scanning calorimetry data for a polymer of the invention.

We have discovered a new class of synthetic crosslinked polymeric materials and blends thereof that may be used to produce surgical devices such as molded devices, drug delivery matrices, coatings, lubricants and the like. The invention also contemplates a process for producing the crosslinked polymers and blends, and methods for utilizing the subject compositions in the pharmaceutical and/or cosemetic treatment of animals.

One aspect of the present invention relates to a polymeric composition comprising one or more recurring monomeric elements in the polymer represented in the general formula (I):

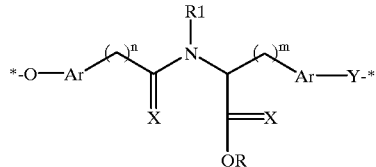

I wherein,
Ar, independently for each occurrence, represents an aryl moiety;
X, for each occurrence, represents O or S (preferably O);
Y represents a phosphate, or derivative thereof;
R represents H, an alkyl, an alkenyl, an alkynyl, an aryl or a heterocycle, preferably a branched or straight chain aliphatic group having from 1–20 carbon atoms;
R1 represents H or a lower alkyl; and
n and m, independently, are 0, 1, 2 or 3 (preferably 1 or 2).

In the above formula, and others used herein, "*" represents another monomeric unit of the polymer, which can be the same or different from I, or a chain terminating group, e.g., a hydrogen or hydroxyl-protecting group, as appropriate.

To further illustrate, Y can be a phosphonamidite, a phosphoramidite, a phosphorodiamidate, a phosphomonoester, a phosphodiester, phosphotriester, a phosphonate, a phosphonate ester, a phosphorothioate, a thiophosphate ester, phosphinate, or a phosphite. A criteria for the selection of Y, as described below, is the desired rate of hydrolysis of the resulting polymer.

The aryl groups, Ar, can be monocyclic or polycyclic groups, which group may be further substituted beyond the backbone of the polymer chain. For instance, the aryl groups can be such groups benzene, pyrrole, furan, thiophene, imidazole, oxazole, thiazole, triazole, pyrazole, pyridine, pyrazine, pyridazine and pyrimidine, and the like.

The group R can essentially be any aliphatic moiety, substituted or unsubstituted, so long as it does not interfere undesirably with the polymerization or biodegradation reactions of the polymer. In preferred embodiments, R is a lower alkyl or an heterocycle.

In other embodiments, R and/or R1 can be selected to permit additional inter-chain crosslinking by covalent or electrostatic (including hydrogen-binding or the formation of salt bridges), e.g., by the use of a sidechain appropriately substituted.

In certain embodiments, it will be desirable for at least 25 percent of the polymer to be composed of monomeric elements shown in Formula I, and even more desirable for at least 50, 77, 85, 90, 95 or even 100 percent of the polymer to be composed of repetitive elements shown in Formula I. The inclusion of other monomeric elements in the polymer, along with the choice of phosphate group, etc., in Formula I, can be used to control the rate of biodegradation of the matrix.

In preferred embodiments, the polymeric chains of the subject compositions, e.g., which include repetitive elements shown in Formula I, have molecular weights of at least 10,000 daltons, more preferably at least 100,000 daltons, and even more preferably at least 250,000 daltons, 500,000 daltons or even at least 1,000,000 daltons.

In preferred embodiments, the polymeric compositions of the present invention include polymeric chains represented in the general formula (Ia)

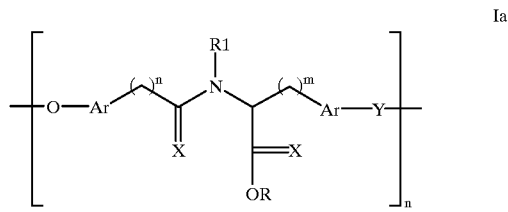

Ia wherein Ar, R, R1, X, Y, n and m are as defined above, and p represents an integer greater than 100, more preferably greater than 1000, and even more preferably greater than 10,000.

In certain examples of the present invention, the polymers and blends can be used as a pharmaceutical carrier in a drug delivery matrix. To form this matrix the polymers and blends would be mixed with a therapeutic agent to form the matrix.

The polymers and blends of the present invention, upon contact with body fluids including blood, spinal fluid, lymph or the like, undergoes gradual degradation (mainly through hydrolysis) with, if so formulated, concomitant release of the dispersed drug for a sustained or extended period (as compared to the release from an isotonic saline solution). This can result in prolonged delivery (over, say 1 to 2,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

2. Definitions

For convenience, certain terms employed in the specification, examples, and appended claims are collected here.

As used herein, the term "aliphatic" refers to a linear, branched, cyclic alkane, alkene, or alkyne. Preferred aliphatic groups in the poly(phosphoester-co-amide) polymer of the invention are linear or branched and have from 1 to 20 carbon atoms.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "heteroatom" as used herein means an atom of any element other than carbon or hydrogen. Preferred heteroatoms are boron, nitrogen, oxygen, phosphorus, sulfur and selenium, and more preferably oxygen, nitrogen or sulfur.

As used herein, the term "aryl" refers to an unsaturated cyclic carbon compound with 4n+2 π electrons, and includes, e.g., 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure, as for example, nitrogen, oxygen, or sulfur, may also be referred to as "aryl heterocycles" or "heteroaromatics." The term "aryl" refers to both substituted and unsubstitited aromatic rings. The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocycle" refer to 4- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathlin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulthydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

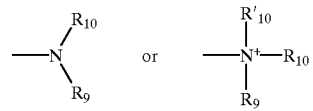

wherein $R_9$, $R_{10}$ and $R'_{10}$ each independently represent a hydrogen, an alkyl, an alkenyl, —$(CH_2)_m$-R80, or $R_9$ and $R_{10}$ taken together with the N atom to which they are attached complete a heterocycle having from 4 to 8 atoms in the ring structure; R80 represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$-R80. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

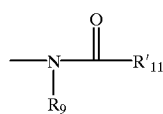

wherein $R_9$ is as defined above, and $R'_{11}$ represents a hydrogen, an alkyl, an alkenyl or —$(CH_2)_m$-R80, where m and R80 are as defined above.

The term "amido" is art recognized as an amino-substituted carbonyl and includes a moiety that can be represented by the general formula:

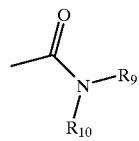

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$-R80, wherein m and R80 are defined above. Representative alkylthio groups include methylthio, ethyl thio, and the like.

The term "carbonyl" is art recognized and includes such moieties as can be represented by the general formula:

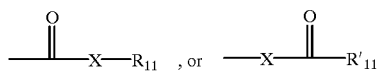

wherein X is a bond or represents an oxygen or a sulfur, and $R_{11}$ represents a hydrogen, an alky, an alkenyl, —$(CH_2)_m$-R80 or a pharmaceutically acceptable salt, $R'_{11}$ represents a hydrogen, an alkyl, an alkenyl or —$(CH_2)_m$-R80, where m and R80 are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O—alkenyl, —O—alkynyl, —O—$(CH_2)_m$-$R_{80}$, where m and R80 are described above.

The terms "sulfoxido", as used herein, refers to a moiety that can be represented by the general formula:

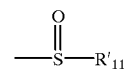

in which $R'_{11}$ is as defined above.

A "sulfone", as used herein, refers to a moiety that can be represented by the general formula:

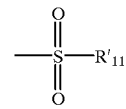

in which $R'_{11}$ is as defined above.

The term "sulfonate" is art recognized and includes a moiety that can be represented by the general formula:

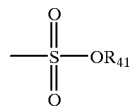

in which $R_{41}$ is an electron pair, hydrogen, alkyl, cycloalkyl, or aryl.

The term "sulfate" is art recognized and includes a moiety that can be represented by the general formula:

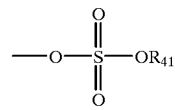

in which $R_{41}$ is as defined above.

The term "sulfonamido" is art recognized and includes a moiety that can be represented by the general formula:

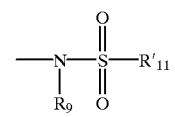

in which $R_9$ and $R'_{11}$ are as defined above.

The term "sulfamoyl" is art-recognized and includes a moiety that can be represented by the general formula:

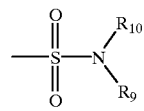

in which $R_9$ and $R_{10}$ are as defined above.

A "phosphoryl" can in general be represented by the formula:

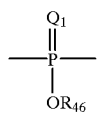

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

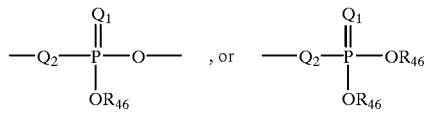

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

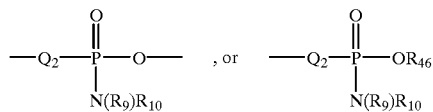

wherein $R_9$ and $R_{11}$ are as defined above, and $Q_2$ represents O, S or N.

A "phosphonarnidite" can be represented in the general formula:

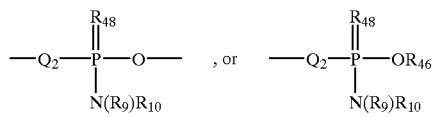

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$-R80, m and R80 being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

Certain monomeric subunits of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

For the purposes of this application, unless expressly noted to the contrary, a named amino acid shall be construed to include both the D or L stereoisomers, preferably the L stereoisomer.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

The phrase "hydroxyl-protecting group" as used herein refers to those groups intended to protect a hydrozyl group against undesirable reactions during synthetic procedures and includes, inter alia, benzyl or other suitable esters or ethers groups known in the art.

As used herein, the definition of each expression, e.g. lower alkyl, m, n, p, etc., when it occurs more than once in any structure, is intended to be independent of its definition elsewhere in the same structure.

3. Exemplary Compositions and Methods

In preferred embodiments, the polymeric composition of the present invention include one or more recurring monomeric elements in the polymer represented in the ageneral formula (II):

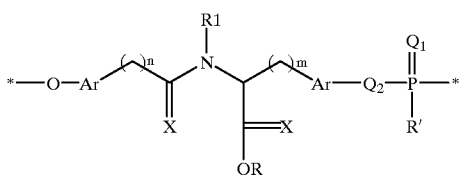

wherein,

Ar, independently for each occurrence, represents an aryl moiety;

X, for each occurrence, represents O or S (preferably O);

$Q_1$ represents O or S;

$Q_2$ represents O, S or NH;

R represents H, an alkyl, an alkenyl, an alkynyl, an aryl or a heterocycle, preferably a branched or straight chain aliphatic group having from 1–20 carbon atoms;

R' represents hydrogen, alkyl, —O-alkyl, aryl, —O-aryl, heterocycle, —O-heterocycle, or —N($R_9$)$R_{10}$;

$R_9$ and $R_{10}$, each independently, represent a hydrogen, an alkyl, an alkenyl, —(CH$_2$)$_i$-$R_{80}$, or $R_9$ and $R_{10}$ taken together with the N atom to which they are attached complete a heterocycle having from 4 to 8 atoms in the ring structure;

$R_{80}$ represents an aryl, a cycloalkyl, a cycloalkenyl, a heterocycle or a polycycle;

$R_1$ represents H or a lower alkyl; and i, n and m, independently for each occurrence, are 0, 1, 2 or 3 (preferably 1 or 2).

Thus, in certain preferred embodiments, the compositions of the present invention include polymeric chains represented in the general formula (IIa)

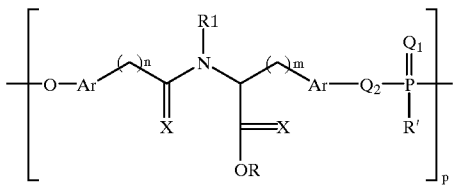

wherein p is in the range of 100–10,000, though it may be greater than 10,000.

In even more preferred embodiments, the biodegradable polymer of the invention comprises the recurring monomeric units shown in formula III:

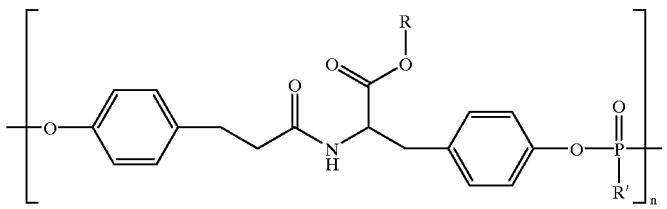

wherein R is selected from the group consisting of H, alkyl, aryl or heterocyclic, preferably a branched or straight chain aliphatic group having from 1–20 carbon atoms. R can be any aliphatic moiety so long as it does not interfere undesirably with the polymerization or biodegradation reactions of the polymer. Specifically, R can be an alkyl group, such as methyl, ethyl, 1,2-dimethylethyl, n-propyl, isopropyl, 2,2-dimethylpropyl or tert-butyl, n-pentyl, tert-pentyl, n-hexyl, n-heptyl and the like; an alkyl group substituent, for example, halogen-substituted alkyl; or a cycloaliphatic group such as cyclopentyl, 2-methylcyclopentyl, cyclohexyl, cyclohexenyl and the like. Preferably, however, R is a branched or straight chain alkyl group and, even more preferably, an alkyl group having from 2 to 18 carbon atoms. Most preferably, R is an n-hexyl group.

R' in the polymer of the invention is an alkyl, alkoxy, aryl, aryloxy, heterocyclic or heterocycl-loxy residue. Examples of useful alkyl R' groups include methyl, ethyl, n-propyl, i-propyl, n-butyl, tert-butyl, —$C_8H_{17}$, and the like groups; alkyl substituted with a non-interfering substituent, such as a halogen group; corresponding alkoxy groups, and alkyl that is conjugated with a biologically active substance to form a pendant drug delivery system.

When R' is aryl or the corresponding aryloxy group, it typically contains from about 5 to about 14 carbon atoms, preferably about 5 to 12 carbon atoms and, optionally, can contain one or more rings that are fused to each other. Examples of particularly suitable aromatic groups include phenyl, phenoxy, naphthyl, anthracenyl, phenanthrenyl and the like.

When R' is heterocyclic or heterocycloxy, it typically contains from about 5 to 14 ring atoms, preferably from about 5 to 12 ring atoms, and one or more heteroatoms. Examples of suitable heterocyclic groups include furan, thiophene, pyrrole, isopyrrole, 3-isopyrrole, pyrazole, 2-isoimidazole, 1,2,3-triazole, 1,2,4-triazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxatriazole, 1,3-oxathiole, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazine, 1,2,4-triazine, 1,2,3-triazine, 1,2,4-oxazine, 1,3,2-oxazine, 1,3,5-oxazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, 1,2-benzopyran, 1,2-benzopyrone, 1,4-benzopyrone, 2,1-benzopyrone, 2,3-benzopyrone, quinoline, isoquinoline, 12,-benzodiazine, 1,3-benzodiazine, naphthpyridine, pyrido[3,4-b]-pyridine, pyrido[3,2-b]-pyridine, pyrido[4,3-b]-pyridine, 1,3,2-benzoxazine, 1,4,2-benzoxazine, 2,3,1-benzoxazine, 3,1,4-benzoxazine, 1,2-benzisoxazine, 1,4-benzisoxazine, carbazole, xanthrene, acridine, purine, and the like.

Preferably, when R' is heterocyclic or heterocycloxy, it is selected from the group consisting of furan, pyridine, N-alkylpyridine, 1,2,3- and 1,2,4-triazoles, indene, anthracene and purine rings.

In a particularly preferred embodiment, R' is an alkyl group, an alkoxy group, a phenyl group, a phenoxy group, or a heterocycloxy group and, even more preferably, an alkoxy group having from 1 to 7 carbon atoms. Most preferably, R' is an ethoxy group.

The number n can vary greatly depending on the biodegradability and the release characteristics desired in the polymer, but typically varies between about 2 and 500. Preferably, n is from about 5 to about 300 and, most preferably, from about 5 to about 200.

Biodegradable polymers differ from non-biodegradable polymers in that they can be degraded during in vivo therapy. This generally involves breaking down the polymer into its monomeric subunits. In certain embodiments, the ultimate hydrolytic breakdown products of a polymer of the invention are desaminotyrosyl tyrosine (which is derived from the naturally occurring amino acid L-tyrosine and its analog, desaminotyrosine, which occurs naturally in plants), an aliphatic alcohol, and phosphate. All of these degradation products are potentially non-toxic. However, the intermediate oligomeric products of the hydrolysis may have different properties. Thus, toxicology of a biodegradable polymer intended for implantation or injection, even one synthesized from apparently innocuous monomeric structures, is typically determined after one or more toxicity analyses.

A typical in vitro toxicity assay would be performed with live carcinoma cells, such as GT3TKB tumor cells, in the following manner:

200 μL of various concentrations of suspensions of the test monomer or polymers are placed in 96-well tissue culture plates seeded with human gastric carcinoma cells (GT3TKB) at $10^4$/well density. The degraded polymer products are incubated with the GT3TKB cells for 48 hours. The results of the assay can be plotted as % relative growth vs. concentration of degraded polymer in the tissue-culture well.

Polymers for use in medical applications such as implants and prostheses can also be evaluated by well-known in vivo tests, such as subcutaneous implantations in rats to confirm that they hydrolyze without significant levels of irritation or inflammation at the subcutaneous implantation sites.

The biodegradable polymer of the invention is preferably sufficiently pure to be biocompatible itself and remains biocompatible upon biodegradation. By "biocompatible" is meant that the biodegradation products or the polymer itself are non-toxic and result in only minimal tissue irritation when implanted or injected into vasculated tissue.

Figure 2:
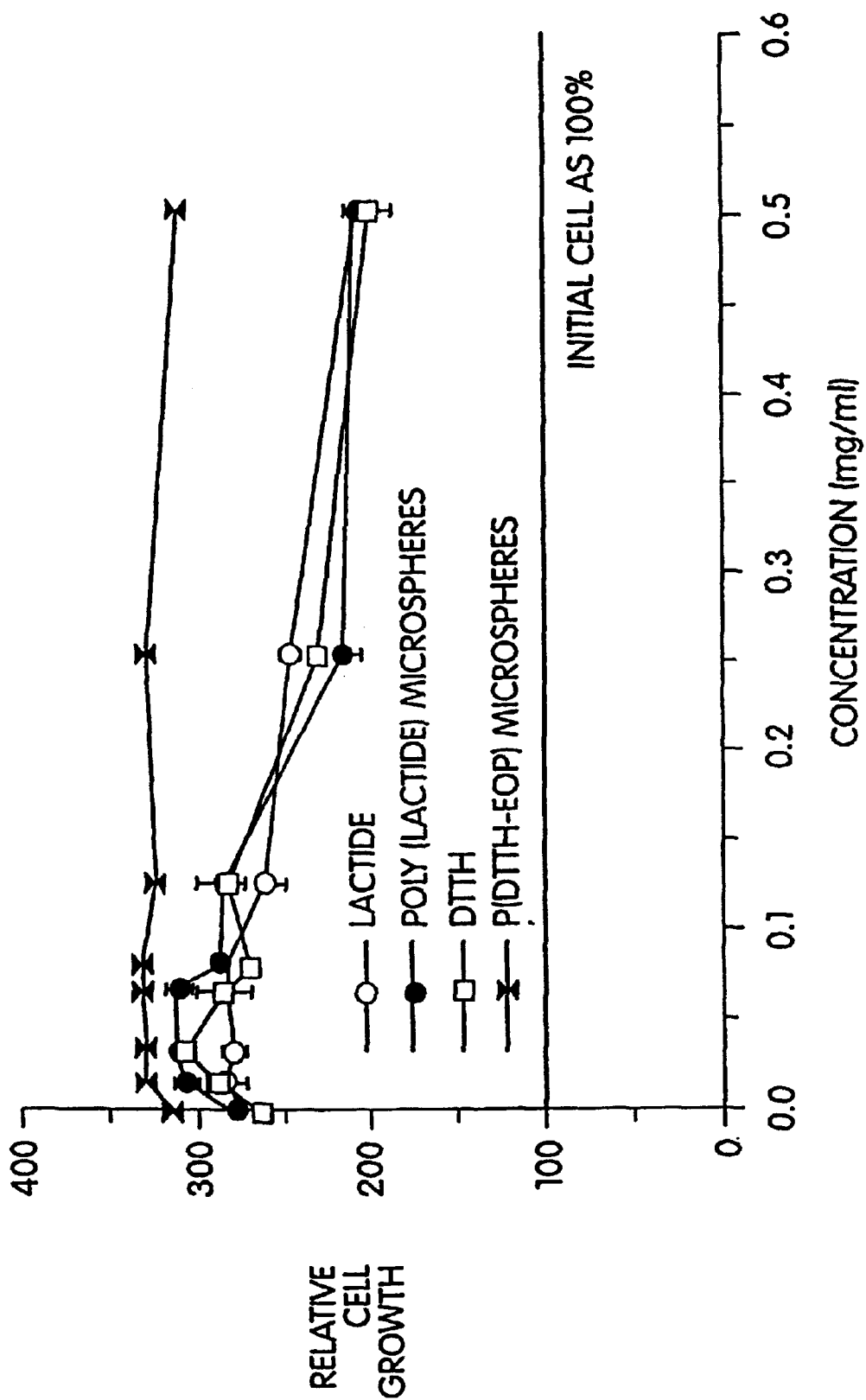
FIG. 2 shows a toxicity assay plot of relative cell growth (%) versus concentration in a tissue-culture well (mg/ml) for four separate polymer samples—DTTH, P(DTTH-EOP), L-lactide and poly(L-lactide).

The in vitro cytotoxicity profile for desaminotyrosyl L-tyrosine hexyl ester ("DTTH"), a monomer used to make a particularly preferred polymer of the invention, and the corresponding polymer P(DTTH-EOP), in microsphere form, as compared with those of a comparison monomer commonly used in biodegradable materials, L-lactide and poly(L-lactide), also in solid and microsphere form, is shown in FIG. 2.

The polymer of the invention is preferably soluble in one or more common organic solvents for ease of fabrication and processing. Common organic solvents include such solvents as ethanol, chloroform, dichloromethane, acetone, ethyl acetate, DMAC, N-methyl pyrrolidone, dimethylformamide, and dimethylsulfoxide. The polymer is preferably soluble in at least one of the above solvents.

The polymer of the invention can also comprise additional biocompatible monomeric units so long as they do not interfere with the biodegradable characteristics desired. Such additional monomeric units may offer even greater flexibility in designing the precise release profile desired for targeted drug delivery or the precise rate of biodegradability desired for structural implants such as for orthopedic applications. Examples of such additional biocompatible monomers include the recurring units found in polycarbonates; polyorthoesters; polyamides; polyurethanes; poly(iminocarbonates); and polyanhydrides.

Synthesis of Poly(phosphoester-co-amide) Polymers

The most common general reaction in preparing poly(phosphates) is a dehydrochlorination between a phosphodichloridate and a diol according to the following equation:

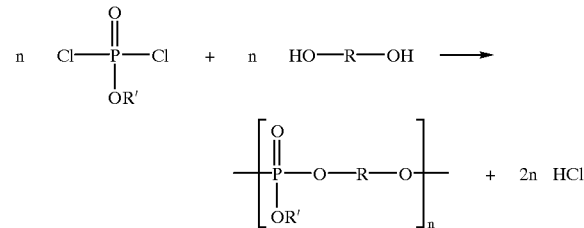

Most poly(phosphonates) are also obtained by condensation between appropriately substituted dichlorides and diols.

Poly (phosphites) have been prepared from glycols in a two-step condensation. A 20% molar excess of a dimethylphosphite is used to react with the glycol, followed by the removal of the methoxyphosphonyl end groups in the oligomers by high temperature.

An advantage of melt polycondensation is that it avoids the use of solvents and large amounts of other additives, thus making purification more straightforward. It can also provide polymers of reasonably high molecular weight. Somewhat rigorous conditions, however, are often required and can lead to chain acidolysis (or hydrolysis if water is present). Unwanted, thermally-induced side reactions, such as crosslinking reactions, can also occur if the polymer backbone is susceptible to hydrogen atom abstraction or oxidation with subsequent macroradical recombination.

To minimize these side reactions, the polymerization can also be carried out in solution. Solution polycondensation requires that both the prepolymer and the phosphorus component be soluble in a common solvent. Typically, a chlorinated organic solvent is used, such as chloroform, dichloromethane, or dichloroethane. The solution polymerization must be run in the presence of equimolar amounts of the reactants and, preferably, a stoichiometric amount of an acid acceptor or a Lewis acid-type catalyst. Useful acid acceptors include tertiary amines as pyridine or triethylamine. Examples of useful Lewis acid-type catalysts include magnesium chloride and calcium chloride. The product is then typically isolated from the solution by precipitation in a non-solvent and purified to remove the hydrochloride salt by conventional techniques known to those of ordinary skill in the art, such as by washing with an aqueous acidic solution, e.g., dilute HCl.

Reaction times tend to be longer with solution polymerization than with melt polymerization. However, because overall milder reaction conditions can be used, side reactions are minimized, and more sensitive functional groups can be incorporated into the polymer. The disadvantages of solution polymerization are that the attainment of high molecular weights, such as a Mw greater than 20,000, is less likely.

Interfacial polycondensation can be used when high molecular-weight polymers are desired at high reaction rates. Mild conditions minimize side reactions. Also the dependence of high molecular weight on stoichiometric equivalence between diol and dichloridate inherent in solution methods is removed. However, hydrolysis of the acid chloride may occur in the alkaline aqueous phase. Sensitive dichloridates that have some solubility in water are generally subject to hydrolysis rather than polymerization. Phase transfer catalysts, such as crown ethers or tertiary ammonium chloride, can be used to bring the ionized diol to the interface to facilitate the polycondensation reaction. The yield and molecular weight of the resulting polymer after interfacial polycondensation are affected by reaction time, molar ratio of the monomers, volume ratio of the immiscible solvents, the type of acid acceptor, and the type and concentration of the chase transfer catalyst.

In a preferred embodiment of the invention, the biodegradable polymer of formula III is made by a process comprising the step of reacting an amino acid derivative known as a desaminotyrosyl L-tyrosine ester, which has the formula IV:

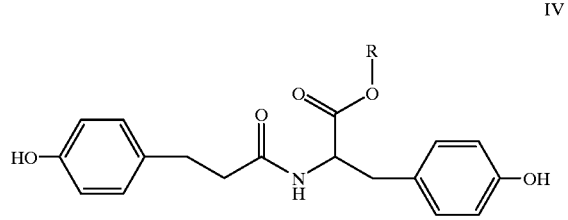
IV wherein R is as defined above, with a phosphodihalidate of formula V:

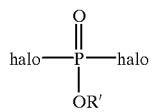
V where "halo" is Br, Cl or I, and R' is as defined above, to form the polymer of formula III.

The desaminotyrosyl L-tyrosine ester of formula IV can be prepared by dicyclohexylcarbodiimide (DCC)-mediated coupling reactions in an inert solvent following standard procedures of peptide chemistry, such as disclosed in Bodanszky, (1984) *Practice of Peptide Synthesis*, 145, the disclosure of which is hereby incorporated by reference. As a specific example, the hexyl ester of desaminotyrosyl L-tyrosine ester ("DTTH") can be prepared by the DCC-mediated coupling of desaminotyrosine and L-tyrosine hexyl ester in tetrahydrofuran as the solvent. The crude alkyl ester is typically obtained as an oil, which can be purified by a number of methods, e.g., flash chromatography on silica gel with 70:30 chloroforn:ethyl acetate or 98:2 methylene chloride:methanol. Crystallization of the pure DTTH can usually be accelerated by crystal seeding.

Alkyl esters of tyrosine having up to eight carbon atoms in the ester group can be prepared by the procedure disclosed in Greenstein et al. (1961), *Chemistry of the Amino Acids*, 929, particularly Illustrative Procedure 10–48, the disclosure of which is hereby incorporated by reference. Alkyl esters of tyrosine having more than eight carbon atoms in the ester group can be prepared according to the procedure disclosed in the examples of Overell, U.S. Pat. No. 4,428,932, which is hereby incorporated by reference.

The purpose of the polymerization reaction of the invention is to form a copolymer comprising (i) desaminotyrosyl L-desaminotyrosine recurring units derived from the amino acid derivative of formula IV and (ii) phosphorylated ester recurring units. The result can be a copolymer having a microcrystalline structure that is particularly well-suited to use as a controlled release carrier.

The process of the invention can take place at widely varying temperatures, depending upon whether a solvent is used and, if so, which one; the molecular weight desired; the susceptibility of the reactants to form side reactions; and the presence of a catalyst. Preferably, however, the process takes place at a temperature ranging from about 0 to about +235° C. for melt conditions. Somewhat lower temperatures, e.g., for example from about −50 to about 100° C. may be possible with solution polymerization or with the use of either a cationic or anionic catalyst.

The time required for the process also can vary widely, depending on the type of reaction being used, the molecular weight desired and, in general, the need to use more or less rigorous conditions for the reaction to proceed to the desired degree of completion. Typically, however, the process takes place during a time between about 30 minutes and 7 days.

While the process may be in bulk, in solution, by interfacial polycondensation, or any other convenient method of polymerization, preferably, the process takes place under solution conditions. Particularly useful solvents include methylene chloride, chloroform, tetrahydrofuran, di-methyl formamide, dimethyl sulfoxide or any of a wide variety of inert organic solvents.

Particularly when solution polymerization reaction is used, an acid acceptor is advantageously present during the polymerization step (a). A particularly suitable class of acid acceptor comprises tertiary amines, such as pyridine, trimethylamine, triethylamine, substituted anilines and substituted aminopyridines. The most preferred acid acceptor is the substituted aminopyridine 4-dimethylaminopyridine ("DMAP").

The polymer of formula III is isolated from the reaction mixture by conventional techniques, such as by precipitating out, extraction with an immiscible solvent, evaporation, filtration, crystallization and the like. Typically, however, the polymer of formula III is both isolated and purified by quenching a solution of polymer with a non-solvent or a partial solvent, such as diethyl ether or petroleum ether.

Biodegradability and Release Characteristics

The polymers of the present invention can, in preferred embodiments, be characterized by a release rate of the biologically active substance in vivo that is controlled at least in part as a function of hydrolysis of the phosphoester bond of the polymer during biodegradation. Additionally, the biologically active substance to be released may be conjugated to the phosphorus sidechain R' to form a pendant drug delivery system. Further other factors are also important.

The life of a biodegradable polymer in vivo also depends upon its molecular weight, crystallinity, biostability, and the degree of crosslinking. In general, the greater the molecular weight, the higher the degree of crystallinity, and the greater the biostability, the slower biodegradation will be.

Accordingly, the structure of the sidechain can influence the release behavior of compositions comprising a biologically active substance. For example, it is expected that conversion of the phosphate sidechain to a more lipophilic, more hydrophobic or bulky group would slow down the degradation process. Thus, release is usually faster from polymer compositions with a small aliphatic group sidechain than with a bulky aromatic sidechain.

The mechanical properties of the polymer are also important with respect to the processability in making molded or pressed articles for implantation. For example, the glass transition temperature can vary widely but must be sufficiently lower than the temperature of decomposition to accommodate conventional fabrication techniques, such as compression molding, extrusion or injection molding. The polymers of the invention typically have glass transition temperatures varying between about 25 to about 75° C. and, preferably, from about 45 to about 65° C.

Weight-average molecular weights (Mw) typically vary from about 2,000 to about 200,000 daltons, preferably from about 2,000 to about 100,000 daltons and, most preferably, from about 2,000 to about 20,000 daltons. Number average molecular weights (Mn) can also vary widely, but generally fall in the range of about 1,000 to 100,000, preferably about 1,000 to 50,000 and, most preferably, from about 1,000 to about 10,000. Intrinsic viscosities generally vary from about 0.01 to about 2.0 dL/g in chloroform at 40° C., preferably from about 0.01 to about 1.0 dL/g and, most preferably, about 0.01 to about 0.5 dL/g.

Polymer Compositions

The polymers of the present invention can be used either alone or as a composition containing, in addition, a biologically active substance to form a variety of useful biodegradable materials. For example, the polymer of formula I can be used to produce a biosorbable suture, an orthopedic appliance or bone cement for repairing injuries to bone or connective tissue, a laminate for degradable or non-degradable fabrics, or a coating for an implantable device, even without the presence of a biologically active substance.

Preferably, however, the biodegradable polymer composition comprises both:

(a) at least one biologically active substance and (b) the polymer having the recurring monomeric units shown in formula I.

The terms "drug," "medicament," or "bioactive substance" (i.e., biologically active substance) as used herein include, biologically, physiologically, or pharmacologically active substances that act locally or systemically in the human or animal body. Various forms of the medicaments or biologically active materials can be used which are capable of being released from the polymer matrix into adjacent tissues or fluids. The medicaments are at least very slightly water-soluble, preferably moderately water-soluble, and are diffusible through the polymeric composition. They can be acidic, basic, or salts. They can be neutral molecules, polar molecules, or molecular complexes capable of hydrogen bonding. They can be in the form of ethers, esters, amides and the like, which are biologically activated when injected into the human or animal body.

The biologically active substance of the invention can vary widely with the purpose for the composition. The active substance(s) may be described as a single entity or a combination of entities. The delivery system is designed to be used with biologically active substances having high-water-solubility as well as with those having low water-solubility to produce a delivery system that has controlled release rates. The term "biologically active substance" includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of useful biologically active substances include the following expanded therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, antigenic materials, and prodrugs.

Specific examples of useful biologically active substances from the above categories include: (a) anti-neoplastics such as androgen inhibitors, antimetabolites, cytotoxic agents, immunomodulators; (b) anti-tussives such as dextromethorphan, dextro-methorphan hydrobromide, noscapine, carbetapentane citrate, and chlophedianol hydrochloride; (c) antihistamines such as chlorpheniramine maleate, phenindamine tartrate, zyrilamine maleate, doxylamine succinate, and phenyltcloxamine citrate; (d) decongestants such as phenylephrine hydrochloride, chenylpropanolamine hydrochloride, pseudoephedrine hydrochloride, and ephedrine; (e) various alkaloids such as codeine phosphate, codeine sulfate and morphine- (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (1) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; (n) anti-infective agents such as anti-fungals, anti-virals, antiseptics and antibiotics; and (o) antigenic materials, particularly those useful in vaccine applications.

To further illustrate, antimetabolites which can be formulated in the subject polymers include, but are not limited to, methotrexate, 5-fluorouracil, cytosine arabinoside (ara-C), 5-azacytidine, 6-mercaptopurine, 6-thioguanine, and fludarabine phosphate. Antitumor antibiotics may include but are not limited to doxorubicin, daunorubicin, dactinomycin, bleomycin, mitomycin C, plicamycin, idarubicin, and mitoxantrone. Vinca alkaloids and epipodophyllotoxins may include, but are not limited to vincristine, vinblastine, vindesine, etoposide, and teniposide.

Nitrosoureas can also be provided in the subject matrizes, including carmustine, lomustine, semustine and streptozocin.

Hormonal therapeutics can also be included in the polymeric matrices, such as corticosteriods (cortisone acetate, hydrocortisone, prednisone, prednisolone, methyl prednisolone and dexamethasone), estrogens, (diethylstibesterol, estradiol, esterified estrogens, conjugated estrogen, chlorotiasnene), progestins (medroxyprogesterone acetate, hydroxy progesterone caproate, megestrol acetate), antiestrogens (tamoxifen), aromastase inhibitors (aminoglutethimide), androgens (testosterone propionate, methyltestosterone, fluoxymesterone, testolactone), antiandrogens (flutamide), LHRH analogues (leuprolide acetate), and endocrines for prostate cancer (ketoconazole).

Other compounds which can be disposed in the polymeric compositions of the present invention include those presently classified as investigational drugs, and can include, but are not limited to alkylating agents such as Nimustine AZQ, BZQ, cyclodisone, DADAG, CB10-227, CY233, DABIS maleate, EDMN, Fotemustine, Hepsulfam, Hexamethylmelamine, Mafosamide, MDMS, PCNU, Spiromustine, TA-077, TCNU and Temozolomide; antimetabolites, such as acivicin, Azacytidine, 5-aza-deoxycytidine, A-TDA, Benzylidene glucose, Carbetimer, CB3717, Deazaguanine mesylate, DODOX, Doxifluridine, DUP-785, 10-EDAM, Fazarabine, Fludarabine, MZPES, MMPR, PALA, PLAC, TCAR, TMQ, TNC-P and Piritrexim; antitumor antibodies, such as AMPAS, BWA770U, BWA773U, BWA502U, Amonafide, m-AMSA, CI-921, Datelliptium, Mitonafide, Piroxantrone, Aclarubicin, Cytorhodin, Epirubicin, esorubicin, Idarubicin, Iododoxorubicin, Marcellomycin, Menaril, Morpholino anthracyclines, Pirarubicin, and SM-5887; microtubule spindle inhibitors, such as Amphethinile, Navelbine, and Taxol; the alkyl-lysophospholipids, such as BM41-440, ET-18-OCH3, and Hexacyclophosphocholine; metallic compounds, such as Gallium Nitrate, CL286558, CL287110, Cycloplatam, DWA2114R, NK121, Iproplatin, Oxaliplatin, Spiroplatin, Spirogermanium, and Titanium compounds; and novel compounds such as, for example, Aphidoicolin glycinate, Ambazone, BSO, Caracemide, DSG, Didemnin, B, DMFO, Elsamicin, Espertatrucin, Flavone acetic acid, HMBA, HHT, ICRF-187, Iododeoxyuridine, Ipomeanol, Liblomycin, Lonidamine, LY186641, MAP, MTQ, Merabarone SK&F104864, Suramin, Tallysomycin, Teniposide, THU and WR2721; a nd Toremifene, Trilosane, and zindoxifene.

Antitumor drugs that are radiation enhancers can also be formulated in the subject polymers. Examples of such drugs include, for example, the chemotherapeutic agents 5'-fluorouracil, mitomycin, cisplatin and its derivatives, taxol, bleomycins, daunomycins, and methamycins.

The pharmaceutical and matrix combinations of the invention may, additionally, be used for the treatment of infections. For such an application, antibiotics, either water soluble or water insoluble, may be immobilized/formulated in the subject polymers. Antibiotics are well known to those of skill in the art, and include, for example, penicillins, cephalosporins, tetracyclines, ampicillin, aureothicin, bacitracin, chloramphenicol, cycloserine, erythromycin, gentamicin, gramacidins, kanamycins, neomycins, streptomycins, tobramycin, and vancomycin The subject polymers can also be formulated with peptide, proteins or other biopolymers, e.g., such as interferons, interleukins, tumor necrosis factor, and other protein biological response modifiers.

Preferably, the biologically active substance is selected from the group consisting of polysaccharides, growth factors, hormones, anti-angiogenesis factors, interferons or cytokines, and pro-drugs. In a particularly preferred embodiment, the biologically active substance is a therapeutic drug or pro-drug, most preferably a drug selected from the group consisting of chemotherapeutic agents and other anti-neoplastics, antibiotics, anti-virals, anti-fungals, anti-inflammatories, anticoagulants, an antigenic materials.

Upon formation of the polymer system, the biologically active material becomes incorporated into the polymer matrix. After implantation of the externally formed polymer system or insertion of a liquid composition to form in situ the polymer system, the bioactive material will be released from the matrix into the adjacent tissues or fluids by diffusion and polymer degradation mechanisms. Manipulation of these mechanisms also can influence the release of the bioactive material into the surroundings at a controlled rate. For example, the polymer matrix can be formulated to degrade after an effective an/or substantial amount of the bioactive material is released from the matrix. Release of a material having a low solubility in water, as for example a peptide or protein, typically requires the degradation of a substantial part of the polymer matrix to expose the material directly to the surrounding tissue fluids. Thus, the release of the biologically active material from the matrix can be varied by, for example, the solubility of the bioactive material in water, the distribution of the bioactive material within the matrix, or the size, shape, porosity, solubility and biodegradability of the polymer matrix, among other factors. The release of the biologically active material from the matrix is controlled relative to its intrinsic rate by varying the polymer molecular weight and by adding a rate modifying agent to provide a desired duration and rate of release.

The biologically active substances are used in amounts that are therapeutically effective. While the effective amount of a biologically active substance will depend on the particular material being used, amounts of the biologically active substance from about 1% to about 65% have been easily incorporated into the present delivery systems while achieving controlled release. Lesser amounts may be used to achieve efficacious levels of treatment for certain biologically active substances.

Other additives can be used to advantage in further controlling the desired release rate of a bioactive material for a particular treatment protocol. For example, if the resulting polymer is too impervious to water, a pore-forming agent can be added to generate additional pores in the matrix. Any biocompatible water-soluble material can be used as the pore-forming agent. These agents can be either soluble in the liquid composition or simply dispersed within it. They are capable of dissolving, diffusing or dispersing out of both the coagulating polymer matrix and the formed polymer system whereupon pores and microporous channels are generated in the matrix and system. The amount of pore-forming agent (and size of dispersed particles of such pore-forming agent, if appropriate) within the composition will directly affect the size and number of the pores in the polymer system.

Pore-formning agents include any pharmaceutically acceptable organic or inorganic substance that is substantially miscible in water and body fluids and will dissipate from the forming and formed matrix into aqueous medium or body fluids or water-immiscible substances that rapidly degrade to water-soluble substances. The pore-forming agent may be soluble or insoluble in the polymer liquid composition of the invention. In the liquid composition of the invention, it is further preferred that the pore-forming agent is miscible or dispersible in the organic solvent to form a uniform mixture. Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and polyvinylpyrrolidone. The size and extent of the pores can be varied over a wide range by changing the molecular weight and percentage of poreforming agent incorporated into the polymer system.

In addition, the polymer composition of the invention can also comprise polymer blends of the polymer of the invention with other biocompatible polymers, so long as they do not interfere undesirably with the biodegradable characteristics of the composition. Blends of the polymer of the invention with such other polymers may offer even greater flexibility in designing the precise release profile desired for targeted drug delivery or the precise rate of biodegradability desired for structural implants such as for orthopedic applications. Examples of such additional biocompatible polymers include other polycarbonates; polyesters; polyorthoesters; polyamides; polyurethanes; poly(iminocarbonates); and polyanhydrides.

Pharmaceutically acceptable carriers may be prepared from a wide range of materials. Without being limited thereto, such materials include diluents, binders and adhesives, lubricants, disintegrants, colorants, bulking agents, flavorings, sweeteners, and miscellaneous materials such as buffers and absorbents in order to prepare a particular medicated composition.

Implants and Delivery Systems Designed for Injection

In its simplest form, a biodegradable therapeutic agent delivery system consists of a dispersion of the therapeutic agent in a polymer matrix. The therapeutic agent is typically released as the polymeric matrix biodegrades in vivo into soluble products that can be excreted from the body.

In a particularly preferred embodiment, an article is used for implantation, injection, or otherwise placed totally or partially within the body, the article comprising the biodegradable polymer composition of the invention. The biologically active substance of the composition and the polymer of the invention may form a homogeneous matrix, or the biologically active substance may be encapsulated in some way within the polymer. For example, the biologically active substance may be first encapsulated in a microsphere and then combined with the polymer in such a way that at least a portion of the microsphere structure is maintained. Alternatively, the biologically active substance may be sufficiently immiscible in the polymer of the invention that it is dispersed as small droplets, rather than being dissolved, in the polymer. Either form is acceptable, but it is preferred that, regardless of the homogeneity of the composition, the release rate of the biologically active substance in vivo remain controlled, at least partially as a function of hydrolysis of the phosphoester bond of the polymer upon biodegradation.

In a preferred embodiment, the article of the invention is designed for implantation or injection into the body of an animal. It is particularly important that such an article result in minimal tissue irritation when implanted or injected into vasculated tissue.

As a structural medical device, the polymer compositions of the invention provide a physical form having specific chemical, physical, and mechanical properties sufficient for the application and a composition that degrades in vivo into non-toxic residues. Typical structural medical articles include such implants as orthopedic fixation devices, ventricular shunts, laminates for degradable fabric, drug-carriers, bioabsorbable sutures, bum dressings, coatings to be placed on other implant devices, and the like.

In orthopedic articles, the composition of the invention may be useful for repairing bone and connective tissue injuries. For example, a biodegradable porous material can be loaded with bone morphogenetic proteins to form a bone graft useful for even large segmental defects. In vascular graft applications, a biodegradable material in the form of woven fabric can be used to promote tissue ingrowth. The polymer composition of the invention may be used as a temporary barrier for preventing tissue adhesion, e.g., following abdominal surgery.

On the other hand, in nerve regeneration articles, the presence of a biodegradable supporting matrix can be used to facilitate cell adhesion and proliferation. when the polymer composition is fabricated as a tube for nerve generation, for example, the tubular article can also serve as a geometric guide for axonal elongation in the direction of functional recovery.

As a drug delivery device, the polymer compositions of the invention provide a polymeric matrix capable of sequestering a biologically active substance and provide predictable, controlled delivery of the substance. The polymeric matrix then degrades to non-toxic residues.

Biodegradable medical implant devices and drug delivery products can be prepared in several ways. The polymer can be melt processed using conventional extrusion or injection molding techniques, or these products can be prepared by dissolving in an appropriate solvent, followed by formation of the device, and subsequent removal of the solvent by evaporation or extraction.

Once a medical implant article is in place, it should remain in at least partial contact with a biological fluid, such as blood, internal organ secretions, mucus membranes, cerebrospinal fluid, and the like.

In more detail, the surgical and medical uses of the filaments, films, and molded articles of the present invention include, but are not necessarily limited to:
a. burn dressings
b. hernia patches
c. medicated dressings
d. fascial substitutes
e. gauze, fabric, sheet, felt or sponge for liver hemostasis
f. gauze bandages g. arterial graft or substitutes
h. bandages for skin surfaces
i. suture knot clip
j. orthopedic pins, clamps, screws, and plates
k. clips (e.g.,for vena cava)
l. staples
m. hooks, buttons, and snaps
n. bone substitutes (e.g., mandible prosthesis)
o. intrauterine devices (e.g., spermicidal devices)
p. draining or testing tubes or capillaries
q. surgical instruments .r. vascular implants or supports
s. vertebral discs
t. extracorporeal tubing for kidney and heart-lung machines
u. artificial skin
v. catheters (including, but not limited to, the catheters described in U.S. Pat. No. 4,883,699 which is hereby incorporated by reference)
w. scaffoldings for tissue engineering applications.

In another embodiment, the aliphatic polyoxaester (including prepolymers and suitable crosslinked polymers and blends) is used to coat a surface of a surgical article to enhance the lubricity of the coated surface. The polymers may be applied as a coating using conventional techniques. For example, the polymers may be solubilized in a dilute solution of a volatile organic solvent, e.g. acetone, methanol, ethyl acetate or toluene, and then the article can be immersed in the solution to coat its surface. Once the surface is coated, the surgical article can be removed from the solution where it can be dried at an elevated temperature until the solvent and any residual reactants are removed. For use in coating applications the polymers and blends should exhibit an inherent viscosity (initial IV in the case of crosslinkable polymers), as measured in a 0.1 gram per deciliter (g/dl) of hexafluoroisopropanol (HFIP), between about 0.05 to about 2.0 dl/g, preferably about 0.10 to about 0.80 dl/g. If the inherent viscosity were less than about 0.05 dl/g (final IV for crosslinked polymers), then the polymer blend may not have the integrity necessary for the preparation of films or coatings for the surfaces of various surgical and medical articles. On the other hand, although it is possible to use polymer blends with an inherent viscosity greater than about 2.0 dl/g, initial IV for crosslinkable polymers), it may be exceedingly difficult to do so.

Although it is contemplated that numerous surgical articles (including but not limited to endoscopic instruments) can be coated with the polymers and blends of this invention to improve the surface properties of the article, the preferred surgical articles are surgical sutures and needles. The most preferred surgical article is a suture, most preferably attached to a needle. Preferably, the suture is a synthetic absorbable suture. These sutures are derived, for example, from homopolymers and copolymers of lactone monomers such as glycolide, lactide, epsilon -caprolactone, 1,4-dioxanone, and trimethylene carbonate. The preferred suture is a braided multifilament suture composed of polyglycolide or poly(glycolide-co-lactide).

The biodegradable polymer particles according to the invention can also advantageously be used for diagnostic purposes. Thus an X-ray contrast agent, such as a poly-iodo aromatic compound, may formulated in the biodegradable polymer of the present invention so that it is liberated and safely eliminated from the body on biodegradation. Such particles may be used for visualisation of the liver and spleen since they are trapped in the reticulo-endothelial systems of those organs. The X-ray contrast agent may also be simply held physically in the polymers by being incorporated during polymerisation.

Polymer particles according to the invention may also contain paramagnetic, superparamagnetic or ferromagnetic substances which are of use in magnetic resonance imaging (MRI) diagnostics. Thus, submicron particles of iron or a magnetic iron oxide can be physically incorporated into the polymers during polymerisation to provide ferromagnetic or superparamagnetic particles. Paramagnetic MRI contrast agents principally comprise paramagnetic metal ions, such as gadolinium ions, held by a chelating agent which prevents their release (and thus substantially eliminates their toxicity). In general many such chelating agents are poly-amino poly-carboxylic acids such as diethylene triamine pentaacetic acid (R. B. Lauffer, Chem. Rev. 87 (1987), pp. 901–927).

Polymer particles of the invention may also contain ultrasound contrast agents such as heavy materials, e.g. barium sulphate or iodinated compounds such as the X-ray contrast agents referred to above, to provide ultrasound contrast media.

EXEMPLIFICATION

The invention now being generally described, it will be more readily understood by reference to the following examples which are included merely for purposes of illustration of certain aspects and embodiments of the present invention, and are not intended to limit the invention.

Example 1
Preparation of the Monomer Desaminotyrosyl L-T-yrosine Hexyl Ester (DTTH)

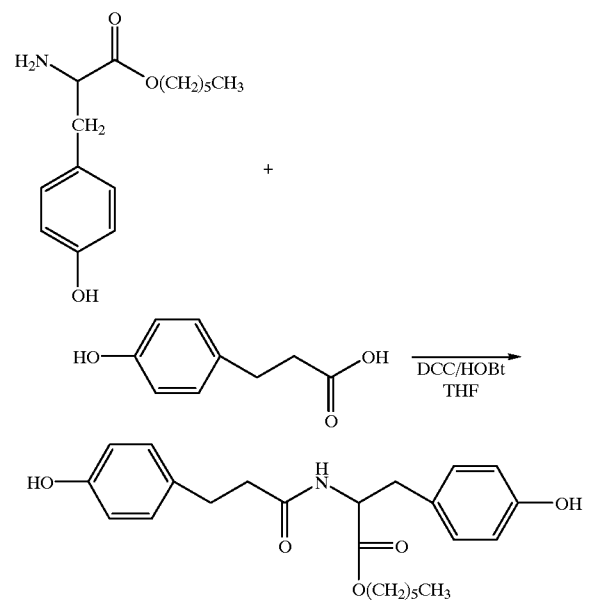

14.15g of desaminotyrosine, 22.6 g of L -tyrosine hexyl ester, and 11.51 g of N-hydroxybenzotriazole hydrate ("HOBt") were dissolved in 150 ml tetrahydrofIran and cooled to −10° C. Di-cyclohexylcarbodiimide (DCC, 19.33 g) was added with stirring.

The reaction mixture was stirred continuously for four hours. Then 5 ml of glacial acetic acid was added to destroy the unreacted DCC, and the mixture was filtered. The filtrate was evaporated to dryness, and the residue was re-dissolved in 150 ml of ethyl acetate, washed with 0.5 N HCl solution (100 ml×3), 0.5 N Na2CO3 solution (100ml×3) , and saturated NaCl solution (100 ml×3), successively. The ethyl acetate solution was dried over anhydrous MgSO4 and evaporated to dryness again.

The crude product was purified by flash column chromatography (CH2Cl2-methanol, 98:2, v/v) . The fractions containing DTTH were evaporated to dryness and redissolved in a small volume of a 95:5 v/v mixture of ethyl acetate-methanol. The DTTH product was gradually crystallized/solidified after an excess of hexane was added. The solid DTTH was removed by filtration and dried under a vacuum to yield about 15–20 g of white powder (43–58% yield).

Example 2
Synthesis of the Corresponding PCH(phosphoester-co-amide) P(DTTH-EOP)

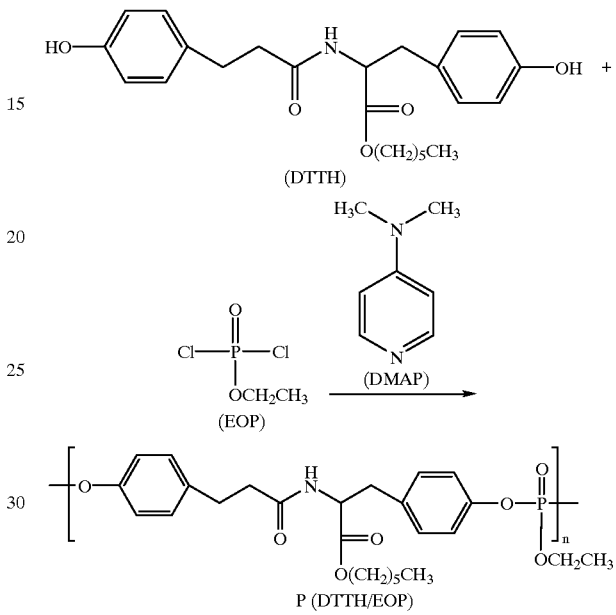

Under an argon stream, 7.8 g of desaminotyrosyl tyrosine hexyl ester (DTTH), 5.07 g of 4-dimethylaminopyridine (DMAP), and 50 ml of methylene chloride were transferred to a 250 ml flask equipped with a funnel. A solution of 3.07 g of ethyl phosphodichloridate (EOP) in 30 ml of methylene chloride was added to the funnel. The solution in the flask was cooled down to −40° C. with stirring, and the EOP solution was added dropwise through the funnel. When the addition was complete, the mixture was gradually brought up to a temperature of 45° C. and was maintained at reflux temperature overnight.

The solvent was then evaporated, and a vacuum (0–1 mm Hg) was applied for one hour while the temperature of the residue was maintained at 120° C. The residue was redissolved in 100 ml of chloroform, washed with a 0.1 M solution of HCl in distilled water, dried over anhydrous Na2SO4, and quenched into 500 ml of ether. The resulting precipitate was collected and dried under vacuum, producing a slightly yellow powder.

Example 3
Properties of P(DTTH-EOP)

A P(DTTH-EOP) polymer was prepared as described above in Example 2. The resulting poly(phosphoester-co-amide) polymer was analyzed by GPC using polystyrene as a standard, and the resulting graph established an Mw of 5,450 and an Mn of 1,670. The polydispersity (Mw/Mn) was determined to be 3.27.

The polymer was very soluble in chloroform, dichloromethane, dimethylformamide, and dimethyl sulfoxide; soluble in N-methylpyrrolidone; and swelled in ethanol, methanol, acetone, acetonitrile and tetrahydrofuran. The intrinsic viscosity was measured in chloroform (CH3Cl) at 40° C. and determined to be 0.055 dL/g.

The Tg of the polymer was determined by differential scanning calorimetry ("DSC") to be 55.6° C., as shown in FIG. 1. No melting peak was observed in the DSC curve.

The invention being thus described, it will be obvious that the same may be varied in many ways. Such variations are not to he regarded as a departure from the spirit and scope of the invention, and all such modifications are intended to be included within the scope of the following claims.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A biodegradable polymer comprising at least about five monomeric units shown in formula I:

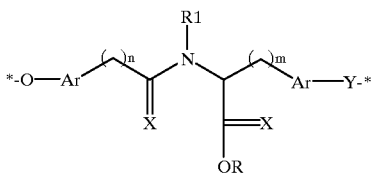

wherein independently for each monomeric unit of said biodegradable polymer:
(a) Ar are independently aryl moieties;
(b) X are independently selected for each occurrence in said monomeric unit from the group consisting of O and S;
(c) Y is selected from the group consisting of phosphonamidite, phosphoramidite, phosphorodiamidate, phosphomonoester, phosphodiester, phosphotriester, phosphonate, phosphonate ester, phosphorothioate, thiophosphate ester, phosphinate, and phosphite;
(d) R and R1 are independently aliphatic groups;
(e) n and m are independently selected from the group consisting of 0, 1, 2 or 3; and
(f) * are independently selected for each occurrence in said monomeric unit from the group consisting of another monomeric unit of said biodegradable polymer and a chain terminating group;
wherein said biodegradable polymer is biocompatible before and upon biodegradation.

2. The biodegradable polymer of claim 1, wherein said biodegradable polymer comprises at least about 100 monomeric units.

3. The biodegradable polymer of claim 1, wherein said biodegradable polymer comprises at least about 1000 monomeric units.

4. The biodegradable polymer of claim 1, wherein said biodegradable polymer comprises at least about 10000 monomeric units.

5. The biodegradable polymer of claim 1, wherein said monomeric units comprise at least about 25% of said biodegradable polymer.

6. The biodegradable polymer of claim 1, wherein said monomeric units comprise at least about 50% of said biodegradable polymer.

7. The biodegradable polymer of claim 1, wherein said monomeric units comprise at least about 77% of said biodegradable polymer.

8. The biodegradable polymer of claim 1, wherein said monomeric units comprise at least about 85% of said biodegradable polymer.

9. The biodegradable polymer of claim 1, wherein said monomeric units comprise at least about 90% of said biodegradable polymer.

10. The biodegradable polymer of claim 1, wherein said monomeric units comprise at least about 95% of said biodegradable polymer.

11. The biodegradable polymer of claim 1, wherein said monomeric units comprise about 100% of said biodegradable polymer.

12. The biodegradable polymer of claim 1, wherein the percentage of said monomeric units of said biodegradable polymer is selected to control the rate of hydrolysis of said biodegradable polymer.

13. The biodegradable polymer of claim 1, wherein said biodegradable polymer comprises additional biocompatible monomeric units.

14. The biodegradable polymer of claim 13, wherein said additional biocompatible monomeric units is one or more of the following types: polycarbonates, polyorthoesters, polyamides, polyurethanes, poly(iminocarbonates), and polyanhydrides.

15. The biodegradable polymer of claim 1, wherein said Y is selected to control the rate of hydrolysis of said biodegradable polymer.

16. The biodegradable polymer of claim 1, wherein both of said occurrences of X in said monomeric units of said biodegradable polymer is either both O or both S.

17. The biodegradable polymer of claim 1, wherein both of said occurrences of X in said monomeric units of said biodegradable polymer is O.

18. The biodegradable polymer of claim 1, wherein both of said occurrences of X in said monomeric units of said biodegradable polymer is S.

19. The biodegradable polymer of claim 1, wherein for more than about 25% of said monomeric units in said biodegradable polymer both of said occurrences of X in said monomeric units is O.

20. The biodegradable polymer of claim 1, wherein for more than about 50% of said monomeric units in said biodegradable polymer both of said occurrences of X in said monomeric units is O.

21. The biodegradable polymer of claim 1, wherein for more than about 75% of said monomeric units in said biodegradable polymer both of said occurrences of X in said monomeric units is O.

22. The biodegradable polymer of claim 1, wherein for about 100% of said monomeric units in said biodegradable polymer both of said occurrences of X in said monomeric units is O.

23. The biodegradable polymer of claim 1, wherein for more than about 25% of said monomeric units in said biodegradable polymer both of said occurrences of X in said monomeric units is S.

24. The biodegradable polymer of claim 1, wherein for more than about 50% of said monomeric units in said biodegradable polymer both of said occurrences of X in said monomeric units is S.

25. The biodegradable polymer of claim 1, wherein for more than about 75% of said monomeric units in said biodegradable polymer both of said occurrences of X in said monomeric units is S.

26. The biodegradable polymer of claim 1, wherein for about 100% of said monomeric units in said biodegradable polymer both of said occurrences of X in said monomeric units is S.

27. The biodegradable polymer of claim 1, wherein said Ar is selected from the group consisting of benzene, pyrrole, furan, thiophene, imidazole, oxazole, thiazole, triazole, pyrazole, pyridine, pyrazine, pyridazine and pyrimidine.

28. The biodegradable polymer of claim 1, wherein each occurrence of said Ar in said monomeric unit is the same.

29. The biodegradable polymer of claim 1, wherein each occurrence said Ar in said monomeric unit is the same for almost all of said monomeric units in said biodegradable polymer.

30. The biodegradable polymer of claim 1, wherein said R is selected from the group consisting of H, alkyl, alkenyl, alkynyl, aryl and heterocycle.

31. The biodegradable polymer of claim 1, wherein said R in said monomeric unit is the same.

32. The biodegradable polymer of claim 1, wherein said R for almost all of said monomeric units in said biodegradable polymer is the same.

33. The biodegradable polymer of claim 1, wherein said R1 is selected from the group consisting of H and lower alkyl.

34. The biodegradable polymer of claim 1, wherein said R1 in said monomeric unit is the same.

35. The biodegradable polymer of claim 1, wherein said R1 for almost all of said monomeric units in said biodegradable polymer is the same.

36. The biodegradable polymer of claim 1, wherein either of said R1 or said R, or both, are capable of forming crosslinkages.

37. The biodegradable polymer of claim 36, wherein said crosslinkages comprise either covalent or electrostatic crosslinkages.

38. The biodegradable polymer of claim 1, wherein each of said n and m for almost all of said monomeric units in said biodegradable polymer is 1.

39. The biodegradable polymer of claim 1, wherein each of said n and m for almost all of said monomeric units in said biodegradable polymer is 2.

40. The biodegradable polymer of claim 1 wherein said biodegradable polymer is prepared by solution polymerization.

41. The biodegradable polymer of claim 1, wherein said biodegradable polymer is at least slightly soluble in at least one of the solvents selected from the group consisting of acetone, dimethylene chloride, chloroform, ethyl acetate, DMAC, N-methyl pyrrolidone, dimethylformamide, and dimethylsulfoxide.

42. A composition comprising the biodegradable polymer of claim 1, wherein the majority of said polymeric chains of said biodegradable polymer of claim 1 have molecular weights of at least about 10,000 daltons.

43. A composition comprising the biodegradable polymer of claim 1, wherein the majority of said polymeric chains of said biodegradable polymer of claim 1 have molecular weights of at least about 100,000 daltons.

44. A composition comprising the biodegradable polymer of claim 1, wherein the majority of said polymeric chains of said biodegradable polymer of claim 1 have molecular weights of at least about 250,000 daltons.

45. A composition comprising the biodegradable polymer of claim 1, wherein the majority of said polymeric chains of said biodegradable polymer of claim 1 have molecular weights of at least about 500,000 daltons.

46. A composition comprising the biodegradable polymer of claim 1, wherein the majority of said polymeric chains of said biodegradable polymer of claim 1 have molecular weights of at least about 1,000,000 daltons.

47. A biodegradable polymer composition comprising: the biodegradable polymer of claim 1, and at least one biologically active substance.

48. The biodegradable polymer composition of claim 47, wherein said biologically active substance is selected from the group consisting of polysaccharides, growth factors, hormones, anti-angiogenesis factors, interferons or cytokines, and pro-drugs of these substances.

49. The biodegradable polymer composition of claim 47, wherein said biologically active substance is a therapeutic drug or pro-drug.

50. The biodegradable polymer composition of claim 47, wherein said biologically active substance is selected from the group consisting of anti-neoplastic agents, antibiotics, anti-virals, anti-fungals, anti-inflammatories, and anticoagulants.

51. The biodegradable polymer composition of claim 47, wherein said biologically active substance and said biodegradable polymer form a homogeneous matrix.

52. The biodegradable polymer composition of claim 47, wherein said biodegradable polymer is characterized by a release rate of the biologically active substance in vivo controlled at least partially as a function of hydrolysis of any Y—O bond in said biodegradable polymer.

53. An article useful for implantation, injection, or otherwise placed totally or partially within the body, said article comprising a biodegradable polymer of claim 1 and a biologically active substance.

54. The article of claim 53, wherein said polymer comprises additional biocompatible monomeric units.

55. The article of claim 53, wherein said biologically active substance is encapsulated within said polymer.

56. The article of claim 53, wherein said article is adapted for implantation or injection into the body of an animal.

57. The article of claim 53, wherein said article results in minimal tissue irritation when implanted or injected into vasculated tissue.

58. The article of claim 53, wherein said article is in the form of a laminate for degradable fabric.

59. The article of claim 53, wherein said article is in the form of a biosorbable suture, a material for repairing bone injuries, or a coating on an implant device.

60. A process for preparing a biodegradable polymer comprising at least about five of the recurring monomeric units of formula I:

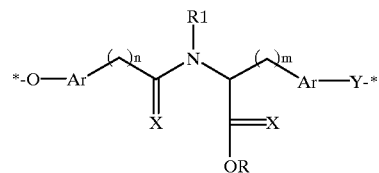

wherein each of said monomeric unit of said biodegradable polymer:

(a) Ar are independently aryl moieties;

(b) X are independently selected for each occurrence in said monomeric unit from the group consisting of O and S;

(c) Y is selected from the group consisting of phosphonamidite, phosphoramidite, phosphorodiamidate, phosphomonoester, phosphodiester, phosphotriester, phosphonate, phosphonate ester, phosphorothioate, thiophosphate ester, phosphinate, and phosphite;

(d) R and R1 are independently aliphatic groups;

(e) n and m are independently selected from the group consisting of 0, 1, 2 or 3; and (f) * are independently selected for each occurrence in said monomeric unit from the group consisting of another monomeric unit of said biodegradable polymer and a chain terminating group; said process comprising reacting an amino acid derivative with a phosphorous-based compound to form the biodegradable polymer of formula I, wherein said biodegradable polymer is biocompatible before and upon biodegradation.

61. The process of claim 60, wherein said process further comprises the step of reacting said biocompatible polymer with additional biocompatible monomeric units.

62. The process of claim 60, wherein said process further comprises combining said biocompatible polymer with one or more of the following: another biocompatible polymer, or a biologically active substance.

63. The process of claim 60, wherein said process takes place at a temperature about 50 to about ±235° C.

64. The process of claim 60, wherein said process takes place during a time between about 30 minutes and seven days.

65. The process of claim 60, wherein said process is a solution polymerization.

66. The process of claim 60, wherein an acid acceptor is present during said process.

67. The process of claim 60, wherein said biodegradable polymer of is purified by quenching a solution of said polymer with a solvent in which said biodegradable polymer is no more than about slightly soluble.

68. A method for the controlled release of a biologically active substance comprising:
   (a) combining a biologically active substance with the biodegradable polymer of claim 1 to form an admixture; and
   (b) administering said admixture at a preselected site in vivo, such that said admixture is in at least partial contact with a biological fluid;
wherein said biologically active substance is controlled released from said admixture.

69. The method of claim 68, wherein said admixture is used as a barrier for adhesion prevention.

70. The method of claim 68, wherein said admixture is fabricated as a tube for nerve generation.

71. The method of claim 68, wherein said admixture is used as a coating for an implant.

72. A biodegradable polymer comprising at least about five monomeric units shown in formula II:

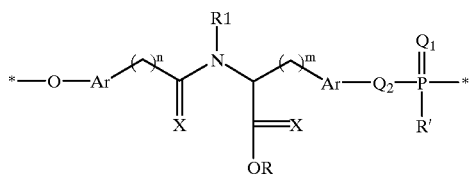

wherein independently for each monomeric unit of said biocompatible polymer:
   (a) Ar are independently aryl moieties;
   (b) X are independently selected for each occurrence in said monomeric unit from the group consisting of O and S;
   (c) Q1 is selected from the group consisting of O and S,
   (d) $Q_2$ is selected from the group consisting of O, S and NE;
   (e) R is selected from the group consisting of H, alkyl, alkenyl, alkynyl, aryl and heterocycle;
   (f) R' is selected from the group consisting of hydrogen, alkyl, —O-alkyl, aryl, —O-aryl, heterocycle, —O-heterocycle, and —N($R_9$)$R_{10}$, wherein $R_9$ and $R_{10}$ are independently selected from the group consisting of hydrogen, alkyl, alkenyl, —$(CH_2)_i$-$R_{80}$, and heterocycle comprising $R_9$, $R_{10}$, said N atom of said N($R_9$)$R_{10}$, and 4 to 8 atoms in the ring structure, wherein $R_{80}$ is selected from the group consisting of aryl, cycloalkyl, cycloalkenyl, heterocycle, and polycycle;
   (g) R1 is selected from the group consisting of H and a lower alkyl;
   (h) n and m are independently selected from the group consisting of 0, 1, 2 or 3; and
   (i) * are independently selected for each occurrence in said monomeric unit from the group consisting of another monomeric unit of said biodegradable polymer and a chain terminating group;
wherein said biodegradable polymer is biocompatible before and upon biodegradation.

* * * * *